United States Patent

Kamiguchi et al.

[11] Patent Number: 4,935,549
[45] Date of Patent: Jun. 19, 1990

[54] PROCESS FOR PRODUCING ACETIC ACID

[75] Inventors: Taiji Kamiguchi; Mutsuo Yamada; Yoshijiro Arikawa; Hirotoshi Tanimoto; Yasuyuki Nishimura, all of Kure, Japan

[73] Assignee: Babcock-Hitachi Kabushiki Kaisha, Tokyo, Japan

[21] Appl. No.: 35,209

[22] Filed: Apr. 6, 1987

Related U.S. Application Data

[63] Continuation of Ser. No. 709,697, Mar. 8, 1985, abandoned.

[30] Foreign Application Priority Data

Mar. 9, 1984 [JP] Japan ................................. 59-44903

[51] Int. Cl.$^5$ ............................................. C07C 51/16
[52] U.S. Cl. .................................... 562/548; 562/536; 568/475
[58] Field of Search ................ 562/548, 536; 709/697; 568/475

[56] References Cited

U.S. PATENT DOCUMENTS 3,213,155 10/1965 Schiesheim et al. .................. 562/544
4,521,631 6/1985 Nishimura et al. .................. 568/478

FOREIGN PATENT DOCUMENTS 58-104291 6/1983 Japan .

Primary Examiner—Werren B. Lone
Attorney, Agent, or Firm—Fay, Sharpe, Beall, Fagan, Minnich & McKee

[57] ABSTRACT

A process for producing acetic acid directly from ethylene under mild conditions is provided, wherein ethylene and oxygen are respectively coordinated with the respective transition metals contained in a specified composite catalyst system, and ethylene activated thereby is successively oxidized by two kinds of oxygen complexes contained in the system and having their electric charge states adjusted, the composite catalyst system comprising a complex represented by a formula (MmXn.Ll) and a complex represented by a formula (M'm'Xn'.L'l') wherein is a transition metal of the groups I, IV~VII and iron group; X, an anion; L, an organic phosphorus compound as a ligand; M', a transition metal of Pt group; L', a nitrile, organic fluorine compound or organic phosphorus compound as a ligand; m, m', n and n', each a number determined by the valences of the transition metals and anion; and l and l' each the number of ligands.

5 Claims, 1 Drawing Sheet

PROCESS FOR PRODUCING ACETIC ACID

This application is a continuation of application Ser. No. 620,336 filed on June 13, 1984 which used as U.S. Pat. No. 4,521,631 on June 4, 1985 which is a continuation of application Ser. No. 709,697 filed Mar. 8, 1985.

BACKGROUND OF THE INVENTION

1. Field of the Invention

This invention relates to a process for producing acetic acid, and more particularly it relates to a process for producing acetic acid by oxidizing ethylene.

1. Description of the Prior Art

Acetic acid is used as raw materials for producing vinyl acetate, acetylcellulose, acetic acid esters, chloroacetic acid, L-lysine, L-glutamic acid, etc. and has occupied an important position as basic chemicals in petrochemical industry.

As conventional processes for producing acetic acid, methanol carbonylation process, lower hydrocarbon (such as n-butene, 1-butene, etc.) oxidization process, and further acetaldehyde oxidization have been practically employed.

Methanol carbonylation process is a new process wherein acetic acid is produced by reacting carbon monoxide with methanol. According to this process, the reaction has been carried out in the presence of a rhodium carbonyl complex as catalyst in liquid phase under conditions of 180° C. and 28 atm to produce acetic acid with a yield of 99 % based on methanol and that of 90 % based on carbon monoxide. However, since rhodium used as catalyst is extremely expensive, it is necessary to make the catalyst loss as small as possible, and further it has been regarded that the economy of the process is dependent on the cost of methanol as raw material (K. Weissermel and H. J. Arpe, Industrial Organic Chemistry, translated by T. Mukaiyama, page 1, 69, Tokyo Kagaku Dohjin (1978)).

According to the process of directly oxidizing lower hydrocarbons, acetic acid is produced at a single stage. However, since the reaction is carried out under relatively high temperatures and pressures of e.g. 150°–200° C. and 20~40 atm, the amount of by-products is so large that a technical problem of improving the reaction selectivity and the yield has been raised. Further, if excess dissolved oxygen is released into the gas phase, hydrocarbons mix with oxygen to have a possibility of troubles such as explosion; hence a countermeasure thereto is required.

On the other hand, according to the acetaldehyde oxidation process, ethylene is oxidized using a catalyst system of palladium chloride ($Pd(2)Cl_2$)-cupric chloride ($Cu(2)Cl_2$) under conditions of 100° C. and 10 Kg/cm² to first produce acetaldehyde, which is further oxidized using a transition metal ion such as ion of Co, Mn, etc. as catalyst to produce acetic acid. In these reactions, $Pd(2)$ ion capable of oxidizing ethylene cannot oxidize the resulting acetaldehyde and hence the catalysts used at the two stages are different to make direct production of acetic acid difficult.

The object of the present invention is to provide a process having overcome these problems and capable of directly producing acetic acid by oxygen-oxidizing ethylene under milder conditions.

SUMMARY OF THE INVENTION

The present invention resides in a process of directly producing acetic acid from ethylene under mild conditions, wherein there is used a composite catalyst consisting of as at least one catalyst component, a transition metal complex capable of forming an oxygen complex by coordination of oxygen molecule with the ion of the transition metal in the complex, and other transition metal complex capable of forming an ethylene complex by coordination of ethylene with the ion of the transition metal in the complex, a modifying ligand being added to the composite catalyst; and ethylene activated by the coordination with the ion of the transition metal is oxidized by the combined oxygen in the oxygen complex having the electric charge state of the combined oxygen adjusted by the addition of the basic compound.

DETAILED DESCRIPTION OF THE PREFERRED EMBODIMENTS

Figure 1:
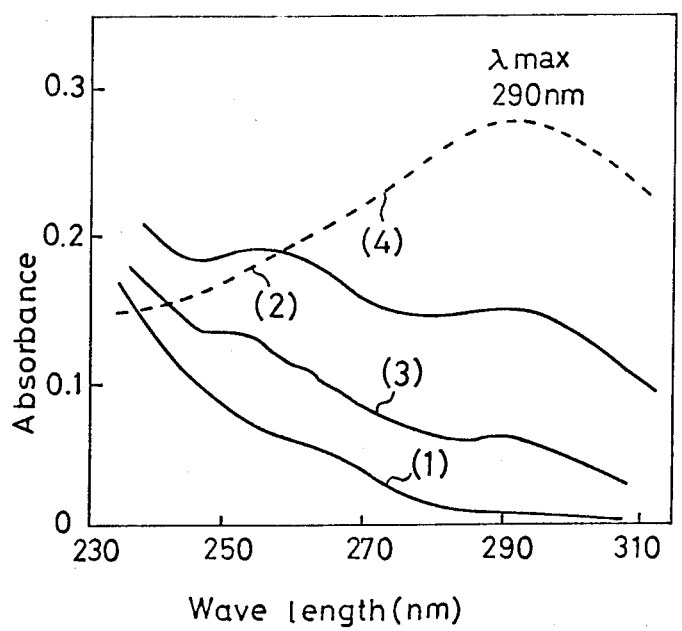
FIG. 1 shows a chart illustrating the absorption spectra of complexes used in the present invention.

The present inventors made extensive research on an oxygen complex as an oxidizing agent effectively functioning for the oxygen-oxidization of ethylene, as previously proposed in Japanese patent application No. Sho 58-104291/1983. As a result, we found that in a representative example, a complex of cuprous chloride ($Cu(1)Cl$) with hexamethylphosphoroamide (hereinafter referred to as hmpa) as a phosphoric acid derivative ($Cu(1)Cl.hmpa$) forms a stable oxygen complex, and further a complex of palladium chloride ($Pd(2)Cl_2$) with acetonitrile ($CH_3CN$) ($Pd(2)Cl_2.CH_3CN$) also forms a stable ethylene complex; and the combined oxygen in the above oxygen complex functions as an effective oxidizing agent for ethylene activated by the above coordination to produce acetaldehyde under a mild condition of the atmospheric pressure. In addition, if the $Cu(1)Cl.hmpa$ is expressed by a general formula $M_mX_n.L_l$, then it corresponds to a case where $m=1$, $n=1$ and $l=1$. Further, for example when $Ti(3)$ or $V(3)$ is a central metal and an anion is $SO_4^{2-}$, the resulting complex is $Ti_2(SO_4)_3.hmpa$ or $V_2(SO_4)_3.hmpa$ and these correspond to a case where $m=2$, $n=3$ and $l=1$, respectively. Still further if the $Pd(2)Cl_2.CH_3CN$ is expressed by a general formula $M'_{m'}X'_{n'}.L'_{l'}$, then it corresponds to a case where $m'=1$, $n'=2$ and $l'=1$. Furthermore when $Pd(2)$ or $I(3)$ is a central metal and $Cl^-$ is an anion, the resulting complex is $Pd(2)Cl_2.CH_3CN$ or $Ir(3)Cl_3.CH_3CN$ and the former corresponds to a case where $m'=1$, $n'=2$ and $l'=1$, while the latter corresponds to a case where $m'=1$, $n'=3$ and $l'=1$.

Further, it is also possible to oxidize acetaldehyde by the combined oxygen in the above oxygen complex to form acetic acid.

As to such oxygen complex, various studies have been made on e.g. copper heme-protein, iron heme-protein, etc. In the case of oxyhemocyanine as the former oxygen complex, it has been clarified that there are present the following three kinds of oxygen complexes wherein the electric charge state of the combined oxygen varies depending on the electric charge transfer between copper ion as the central metal ion in the oxygen complex and oxygen:

$$Cu(1)-O_2-Cu(1) \quad (i)$$

$$\text{Cu(1)-O}_2{}^- \text{-Cu(2)} \qquad \text{(ii)}$$

$$\text{Cu(2)-O}_2{}^{2-}\text{-Cu(2)} \qquad \text{(iii)}$$

The complex (i) has been referred to as an oxygen complex without any electric charge transfer i.e. oxo complex, the complex (ii), superoxo complex, and the complex (iii), peroxo complex. In addition, when the electric charge states of the combined oxygen in the respective complexes are noted, it is considered that the combined oxygen in the case of (i) functions as an electrophilic oxidizing agent since there is no electric charge transfer, while the combined oxygen in the case of (ii) nucleophilically reacts with an organic substrate to oxidize it since oxygen functions as a superoxo ion.

Further, as to iron hem complexes, too, similar studies have been made, and it has been regarded that as to the combined oxygen, oxygen complexes having different electric charge states are formed as follows:

$$\text{Fe(2)}-\text{O}_2-\text{Fe(2)} \qquad \text{(iv)}$$

$$\text{Fe(2)}-\text{O}_2-\text{Fe(3)} \qquad \text{(v)}$$

$$\text{Fe(2)}-\text{O}_2{}^{2-}-\text{Fe(3)} \qquad \text{(vi)}$$

It is considered that such oxygen complexes having a protein as a ligand are stable inside living bodies and there is carried out an oxidation reaction corresponding to the respective electric charge states of the combined oxygen activated by the coordination so that the reaction heat generated by the reaction constitutes the energy source of living bodies. However, these complexes are unstable such that for example, in the case of the oxygen complex of the iron hem-protein, if this complex is separated from the inside of the living bodies, Fe(2) is oxygen-oxidized into Fe(3) within 30 seconds at room temperature by the combined oxygen. However, it has been observed that in dimethylsulfoxide as a basic solvent, the oxygen complex in the state (iv) can be existent for about 20 minutes at 20° C.

In view of the electric charge states of the oxygen complexes inside living bodies, as well as other facts, it is considered that in the new oxygen complexes found by the present inventors, too, a similar intramolecular electric charge transfer may occur.

Various studies have been made on the above reaction wherein ethylene activated by the coordination with the Pd(2) complex is oxidized by the combined oxygen in the oxygen complex to produce acetaldehyde. As a result, since the oxidation reaction proceeds electrophilically, it is considered that a usual combined oxygen in the oxygen complex without any intramolecular electric charge transfer as shown in the following equation (hereinafter the ligand hmpa being abbreviated to L) functions as an effective oxidizing agent:

$$\text{L.ClCu(1)-O}_2\text{-Cu(1)Cl.L} \qquad \text{(1)}$$

On the other hand, in the oxidation reaction of acetaldehyde into acetic acid, oxygen nucleophilically reacts with the carbonyl carbon of acetaldehyde. Namely it is considered that a superoxo complex ($-\text{O}_2{}^-$—) of an intramolecular electric charge transfer type is effective as shown in the following equation:

$$\text{L.ClCu(1)}-\text{O}_2{}^-\!-\text{Cu(2)Cl.L} \qquad \text{(2)}$$

Now we have found that as to the above oxygen complex used for the oxygen-oxidation of ethylene, it is possible to adjust its intramolecular electric charge state by adequately making a basic solvent such as sulfolane coexistent therewith. Namely, it has become possible to make a usual oxo complex and a superoxo complex coexistent in a suitable proportion. This is an important finding in the direct production of acetic acid from ethylene, as described above. The reaction is shown by the following equations:

$$\text{L.ClCu(1)-O}_2-\text{Cu(1)Cl.L} + 2\text{Pd(2)Cl}_2.\text{C}_2\text{H}_4.\text{CH}_3\text{CN} + \qquad (3)$$

$$2\text{L} \longrightarrow 2\text{CH}_3\text{CHO} + 2\text{Cu(1)Cl.L} + 2\text{Pd(2)Cl}_2.\text{CH}_3\text{CN.L}$$

$$2\text{CH}_3\overset{\text{O}}{\underset{\|}{\text{CH}}} + \text{L.ClĊu(1)-O}_2{}^-\!-\text{Cu(2)Cl.L} \longrightarrow \qquad (4)$$

$$2\text{CH}_3\text{COOH} + 2\text{Cu(1)Cl.L}$$

$$\text{CH}_2\!=\!\text{CH}_2 \xrightarrow{\frac{1}{2}\text{O}_2} \text{CH}_3\text{CHO} \xrightarrow{\frac{1}{2}\text{O}_2} \text{CH}_3\text{COOH} \qquad (5)$$

As to the reaction equations, two reactions of acetaldehyde formation and acetic acid formation through its oxidation are separately denoted above, but if the reactions are expressed by a general equation, the reactions proceed successively as shown by the equation (5), to make it possible to produce acetic acid directly from ethylene by means of catalysts having the same composition but being different only in the electric charge state.

The fact to be noted in the above reactions is that the reactions can proceed in the presence of catalysts which, however, are of the same kind in view of their compositions. Namely, as to the oxygen complex in the above catalyst solution, two kinds of oxygen complexes having different electric charge states are formed and ethylene activated by coordination with Pd(2) complex is oxygen-oxidized into acetaldehyde by the activated combined oxygen in the oxygen complex of oxo type (L.ClCu(1)—O$_2$—Cu(1)Cl.L), and the resulting acetaldehyde is successively nucleophilically oxygen-oxidized by the activated oxygen in the superoxo complex (L.ClCu(1)—O$_2{}^-$—Cu(2)Cl.L) to obtain acetic acid; thus it is possible to successively oxygen-oxidize ethylene in the presence of catalysts having the same composition to produce acetic acid.

In addition, according to the conventional process of oxidizing ethylene by means of the oxidizing force of a Pd(2) ion, it is well known that Pd(2) ion does not have any capability of successively oxidizing ethylene, but another catalyst such as Co ion or Mn ion, etc. is required and two separate reactors are provided, that is, acetic acid is produced according to a two-stage process. Accordingly the above process is entirely different from that of the present invention.

Now, as to the adjustment of the intramolecular electric charge transfer in the oxygen complex, a basic (election donative) compound (sulfolane in a representative example) was added in various amounts to the above oxygen complex solution, followed by measuring the change in the ultraviolet absorption spectra thereof in ethanol at 30° C. The results are shown in FIG. 1. The curve (1) in FIG. 1 refers to the spectrum in the case where sulfolane was made present in amounts of 8 mols/l or more. In this case, the spectrum was constant for a long time and no change in the spectrum was observed. In this case, it is considered that usual oxygen molecule was present in the complex solution in the form of an oxygen complex wherein the molecule was coordinated with the metal ion i.e. the oxo complex (i). On the other hand, in the absence of sulfolane, change with lapse of time was observed and ultimately such spectrum as shown by a curve (2) in FIG. 1 was obtained. Further, when the sulfolane concentration was made 2 mols/l, a spectrum as shown by a curve (3) in FIG. 1 was obtained, which corresponded to intermediate spectra between the above two. For comparison, spectrum of divalent copper complex ($Cu(2)Cl_2.L$) under the same conditions was measured. As a result, the spectrum was entirely different from that of the oxygen complex, as shown by a curve (4) in FIG. 1, and even when sulfolane was added, no change in spectra was observed.

In view of the results of the above comparison studies of spectra, the spectra of (2) and (3) in FIG. 1 show formation of a superoxo complex of electric charge transfer type. This superoxo complex is an indispensable component for nucleophilically oxidizing the resulting acetaldehyde.

Thus, we have found that it is possible to adjust the proportion of the oxo complex and the superoxo complex present, having different electric charge states, and effective for ethylene oxidation and oxidation of the resulting acetaldehyde, respectively, depending on the amount of a basic solvent represented by sulfolane added.

Such an effectiveness of electron donative compounds represented by sulfolane is considered to be due to the fact that the compounds solvate (or coordinate with) the metal ion in the oxygen complex to change the electric charge state of the metal ion and thereby inhibit the electric charge transfer to oxygen and as a result, suppress formation of the superoxo complex. Thus, this fact accords with the above example of study on the iron-protein.

Now, when the superoxo complex is absent in the catalyst solution by the addition of e.g. sulfolane, oxidation of acetaldehyde into acetic acid will no longer occur. Thus, as for the combined oxygen in the oxygen complex, it is necessary that two kinds of the usual oxo complex and the superoxo complex are present in admixture, and in an example represented by sulfolane, it is necessary that its amount added by 8 mols/l or less, as described later in comparative examples In addition, when an electron donative substance is present, it is not observed that the oxo oxygen complex changes via the superoxo complex and further oxygen-oxidizes Cu(1) as the central metal into Cu(2). Thus the oxo oxygen complex is stable. Further, even when an electron donator is absent, oxygen-oxidization of Cu(1) into Cu(2) with the combined oxygen is such that boiling at 100° C. is required.

As described above, when the amount of an electron donative substance (represented by sulfolane) added is adjusted, an oxo complex and a superoxo complex are made present in admixture in the form of the combined oxygen and ethylene is passed therethrough, then ethylene is coordinated with Pd(2) complex and activated thereby so that it is oxygen-oxidized according to an electrophilic reaction by means of the combined oxygen in the oxo complex The resulting acetaldehyde is successively oxygen-oxidized into acetic acid according to a nucleophilic reaction of the superoxo complex with the carbonyl carbon of acetaldehyde.

Namely, according to the present invention, it has become possible that ethylene coordinated with Pd(2) and activated thereby is oxygen-oxidized by oxygen molecule coordinated with Cu(1) complex and activated thereby to produce acetaldehyde as an intermediate product, which is successively oxygen-oxidized to produce acetic acid from ethylene with a solution of catalysts having the same composition in an ultimately one-stage reactor. As seen from the gist of the present invention described above, the present production process is directed to a process wherein ethylene is oxidized into acetaldehyde by means of an oxidizing force of a Pd(2) ion and the resulting acetaldehyde is then oxidized into acetic acid by means of other kind of catalyst, that is, a process which is entirely different from conventional processes such as a process employing two reaction columns.

In addition, in the present production process, when the resulting product is separated from the catalyst solution by means of an operation such as distillation, followed by passing air or oxygen through the resulting catalyst solution, the oxygen complex is again formed to make it possible to repeatedly use the resulting catalyst solution as the catalyst for oxidizing ethylene and acetaldehyde as an intermediate product. Further, Pd(2) complex also repeatedly functions as a catalyst for activating ethylene.

Now, the $M_mX_n$ in the $M_mX_n.L$ as the complex catalyst capable of forming an oxygen complex in the present composite catalyst system, refers to salts of a transition metal such as Cu and Ag of the group I, Ti and Zr of the group IV, V and Nb of the group V, Cr, Mo and W of the group VI, Mn of the group VII and Fe, Co and Ni of the group VIII, each of the Periodic Table, preferably halides of Cu(1), Ti(3) and V(3). As for the ligand L, suitable examples thereof are phosphoric acid derivatives such as triphenylphosphine oxide, hexamethylphosphoramide and mono-, di- and triesters formed by reaction of phosphoric acid with methanol, ethanol, etc. and further dimethyl methylphosphonate, and methyl dimethylphosphinate, and further phosphorous acid derivatives such as mono-, di- and triesters formed by reaction of phosphorous acid with methanol, ethanol, etc. and phenylphosphinous acid esters, dimethylphosphinic acid esters, and organic phosphorus compounds represented by triethylphosphine and triphenylphosphine. Among these, hexamethylphosphoramide is particularly preferable.

Further, as the basic (electron donative) compounds used for adjusting the proportion of the intramolecular electric charge transfer in the oxygen complex, dimethylsulfolane, dimethylsulfoxide, dimethylformamide, dimethylsulfone, trimethylmethane, etc. are preferable in addition to the above sulfolane.

On the other hand, as the $M'_{m'}X_{n'}$ in the complex catalyst ($M'_{m'}X_{n'}.L'$) capable of forming the ethylene complex, salts of lower valence ion of transition metals belonging to platinum group of the group VIII of the Periodic Table are suitable, and as the ligand L', nitriles such as acetonitrile, propionitrile, benzonitrile, tolunitrile, etc. and the above organic phosphorus compounds and further, organic fluorine compounds such as fluorinated toluene, benzotrifluoride, etc. are suitable. Among these, nitriles are particularly preferable.

In addition, as a solvent used in the case where the reaction is carried out in solution state, those which dissolve the composite catalyst and at the same time are easy to separate from the resulting acetic acid (b.p. 118° C./ 760 mmHg) are preferable, and at least one kind of solvents selected from those such as ethylene glycol, diglyme, dioxane, chlorobenzene, propylenecarbonate, N-methylphrrolidone, butyrolactone and hydrocarbons having carbon atoms in the vicinity of 10, or mixtures of the foregoing are used. Further, in the case where the ligand L or L' is liquid, these may be themselves used as the solvent.

Further, it is also possible to have the composite catalyst supported on active carbon, silicates or porous glass or a porous carrier such as polymers having a macroreticular structure to produce acetic acid by oxygeneoxidizing ethylene in the presence of the resulting material.

In addition, even when acetaldehyde as an intermediate product is coexistent with acetic acid, it is possible to easily separate acetaldehyde from acetic acid; hence no particularly serious problem is raised. This makes it possible to produce acetic acid and acetaldehyde at the same time.

Embodiments of direct production reaction of acetic acid by way of ethylene oxidation according to the present invention have been described above. Next the present invention will be described in more detail by way of Examples.

EXAMPLE 1

Into a 1.2 l capacity autoclave were fed Cu(1)Cl (10 g, 0.1 mol) and hmpa (350 g, 2.0 mols) to prepare a Cu(1)Cl.hmpa complex solution. Further into a test tube with ground stopper were fed Pd(2)Cl$_2$(2.7 g, 15 mmols) and CH$_3$CN(513 g, 12.5 mols) to prepare a Pd(2)Cl$_2$.CH$_3$CN complex solution, which was then transferred into the reactor to prepare a catalyst solution (Cu(1)Cl.hmpa/Pd(2)Cl$_2$.CH$_3$CN hmpa/hmpa, CH$_3$CN system) (1 l) containing 0.1 mol/l of Cu(1)Cl and 0.015 mol/l of Pd(2)Cl$_2$. When air (1.5 l) was passed through the catalyst solution at 25° C. under the atmospheric pressure, oxygen (250 ml, 11 mmols) was absorbed to obtain a solution having an oxygen complex concentration of 0.011 mol/l. Thereafter, passing of nitrogen gas or degassing by heating was carried out. As a result, only oxygen in the gas part of the reactor and oxygen physically dissolved in the liquid phase were removed, but elimination of oxygen from the combined oxygen in the oxygen complex was not observed; thus it was confirmed that the oxygen absorption through formation of the oxygen complex was irreversible. This is a great specific feature in respect of the safety of driving operation in practical process.

After these operations, ethylene (3 l) was passed at 25° C. under the atmospheric pressure, 2.2 l of ethylene was absobed and the ethylene concentration became 0.09 mol/l. The reactor was then closed and just thereafter warmed up to 60° C., followed by reacting the materials for 2 hours and analyzing the product according to gas chromatography to form acetic acid (0.2 g) and acetaldehyde (0.6 g). In this system, the ethylene complex was present in excess of the oxygen complex and also the reaction was carried out according to the above equations (3) and (4); thus the acetic acid yield was 32 % and the acetaldehyde yield was 67 %, each based on the combined oxygen in the oxygen complex. In addition, the acetic acid concentration in the product was 25 % by weight, but it was possible to easily separate the acid from acetaldehyde by distillation and thereby raise its purity.

EXAMPLE 2

Operations and reaction were carried out as in Example 1 except that the reaction temperature was lowered to 40° C. As a result, acetic acid (0.1 g) and acetaldehyde (0.8 g) were formed. The acetic acid yield was 15 % and the acetaldehyde yield was 85 %, each based on the combined oxygen. Namely if the reaction temperature is too low, acetaldehyde becomes a main product.

EXAMPLE 3

Operations and reaction were carried out as in Example 1 except that acetonitrile was replaced by benzonitrile (660 g). As a result, acetic acid (0.3 g) and acetaldehyde (0.4 g) were obtained. The acetic acid yield was 50 % and the acetaldehyde yield was 45 %; the acetic acid concentration in the product increased to 43 %.

EXAMPLE 4

Operations were carried out as in Example 3 except that the reaction temperature was raised to 80° C. As a result, acetic acid (0.4 g) and acetaldehyde (0.3 g) were obtained. The yields of acetic acid and acetaldehyde were 60 % and 35 %, respectively.

EXAMPLE 5

In Example 1, the composition of the composite complex catalyst was made the same as in Example 3, and the oxygen complex concentration and the ethylene complex concentration were made 0.04 mol/l (900 ml in terms of the combined oxygen) and 0.02 mol/l (450 ml in terms of ethylene), respectively. Thereafter operations were carried out as in Example 1 and reaction was carried out at 80° C. for 4 hours, to obtain acetic acid (0.6 g). In this system, the oxygen complex was present in excess of the ethylene complex and also the reaction was carried out according to the above equations 3) and 4); thus the acetic acid yield based on ethylene was 49 %. In addition, the acetaldehyde yield was 49 %, but the amount of other by-products was below the detection limit.

EXAMPLE 6

The same concentrations of the oxygen complex and the ethylene complex were formed as in Example 5 except that hmpa (100 g) and benzonitrile (660 g) were added and further sulfolane (240 g, 2.0 mols/l) was used. Thereafter reaction was carried out under the same conditions as in Example 5 to obtain acetic acid (1.2 g). The acetic acid yield based on ethylene was 98 %. In addition the acetaldehyde yield was 2 % and the amount of other by-products was below the detection limit. The acetic acid concentration was nearly 98 %.

Taking account of the above-mentioned results according to the absorption spectra at the same time, when sulfolane as a basic substance was added in 2 mols/l to the catalyst solution, the above oxo complex (L.Cu(1)Cl—O$_2$—CuCl(1)Cl.L) and superoxo complex (L.Cu(1)Cl.O$_2^-$.Cu(2)Cl.L) were present in adequate amounts, to oxidize ethylene into acetaldehyde through the electrophilic reaction by means of oxygen in the oxo complex and successively oxidize the resulting acetaldehyde into acetic acid through the nucleophilic reaction by means of oxygen in the latter complex whereby a high acetic acid yield was obtained as in this Example. Namely the fact that the oxo complex and the superoxo complex are present in admixture in adequate amounts is an important point in the present invention and the coexistence of a basic compound represented by sulfolane is a great specific feature.

On the other hand, the experiment of this Example was repeatedly carried out, but there was observed no oxygen-oxidation of copper ion in the oxygen complex into divalent copper ion. This is considered to be due to the effectiveness of stabilizing the oxygen complex by means of sulfolane as a basic compound. The basic compound has functions of adjusting the electric charge transfer in the oxygen complex and at the same time stabilizing the complex. In addition, this case is directed to a non-aqueous solution system, but almost the same results were obtained even in the coexistence of 1 % of $H_2O$, and the presence of a water content of 4 to 5 % without any coexistence of CuCl does not raise any problem.

EXAMPLE 7

The same composite catalyst solution was prepared as in Example 6, and air and ethylene outside the explosion limit were at the same time passed through the solution at a rate of amount of reaction solution/gas passing rate of 15 $h^{-1}$. As a result, 37 % of ethylene was converted into acetic acid.

EXAMPLE 8

Operations and reaction were carried out as in Example 6 except that Pd(2)Cl$_2$ was replaced by Pt(2)Cl$_2$ (8 g, 0.03 mol). As a result the acetic acid yield was 98 % and the aceitc acid concentration in the product was also nearly 100 %.

EXAMPLE 9

Reaction was carried out under the same conditions as in Example 6 except that Cu(1)Cl was replaced by cuprous bromide (Cu(1)Br). The acetic acid yield was 92 %. Further, when Cu(1)Cl was replaced by cuprous iodide, the acetic acid yield was 94 %.

EXAMPLE 10

Reaction was carried out as in Example 8 except that Pt(2)Cl$_2$ was replaced by platinum bromide (Pt(2)Br$_2$) and Cu(1)Cl was replaced by Cu(1)Br. The acetic acid yield was 93 %.

EXAMPLE 11

Operations were carried out as in Example 6 except that benzonitrile was replaced by benzotrifluoride. The acetic acid yield was 92 %.

EXAMPLE 12

Example 6 was repeated except that the amount of benzonitrile was reduced to 100 g and xylene (560 g) was added to study the effect of solvent. The acetic acid yield was 97 %, that is, almost the same as that in Example 6.

EXAMPLE 13

Operations and reaction were carried out as in Example 6 except that hmpa was replaced by phosphoric acid triphenyl ester. As a result the acetic acid yield was 94 %, that is, almost the same as that in Example 6.

EXAMPLE 14

Operations were carried out as in Example 6 except that air was replaced by pure oxygen. No significant differences in the oxygen complex concentration and the ethylene complex concentration in the solution were observed. Further, reaction was carried out under the same conditions as those in Example 6. The acetic acid yield was 98 % and its concentration in the product was more than 98 %. Thus, in the present invention, the oxygen source is unnecessary to be pure oxygen, but cheap air is sufficient.

EXAMPLE 15

Operations were carried out as in Example 6 except that Cu(1)Cl was replaced by V(3)Cl$_3$ and V(3)Cl$_3$ was used in 0.1 mol/l to form 0.014 mol/l of an oxygen complex (310 ml in terms of the combined oxygen) and 0.01 mol/l of ethylene complex (220 ml in terms of ethylene), and reaction was carried out under the same conditions as in Example 6. As a result, acetic acid (0.3 g) was formed and its yield based on ethylene was 52 %.

EXAMPLE 16

Operations were carried out as in Example 6 except that Cu(1)Cl was replaced by Ti(3)Cl$_3$ and Ti(3)Cl$_3$ was used in 0.1 mol/l to form 0.03 mol/l of an oxygen complex and 0.02 mol/l of an ethylene complex, and reaction was carried out under the same conditions as in Example 6. As a result, acetic acid (0.7 g) was formed and its yield based on ethylene was 61 %.

EXAMPLE 17

In Example 6, Cu(1)Cl, Pd(2)Cl$_2$, hmpa, benzonitrile and sulfolane were at the same time added to the reactor. As a result, a uniform solution was obtained, and reaction was carried out as in Example 7. No significant difference in the conversion of ethylene into acetic acid was observed. Thus, it was found that in the present invention, step-wise operations as shown in Example 1 are not always required.

EXAMPLE 18

Beads of a macro-reticular type styrene-divinylbenzene copolymer (particle diameter 1 mm$\phi$; specific surface area 700~800 m$^2$/g; Amberlite XAD-4 manufactured by Organo Co.) (50 ml) were impregnated with a catalyst solution containing the oxygen complex of the composition shown in Example 8, followed by filtering by suction to prepare a granular catalyst, which was then filled in a hard glass reaction tube having an inner diameter of 20 mm$\phi$ and heated to 120° C., followed by passing ethylene at a rate of 1 l/min. (SV 1,200 $h^{-1}$) through the catalyst and analyzing the product in the exit gas according to gas chromatography. As a result the products consisted only of acetic acid and acetaldehyde and the acetic acid yield based on ethylene was 2 % since start of the reaction till the succeeding 2 hours. Thereafter the exit gas was recycled to give an acetic acid yield amounting to 60 % based on the oxygen complex. Ethylene feed was once stopped and the catalyst was cooled down to 60° C., followed by passing air to regenerate the combined oxygen consumed by the reaction, and again repeating the oxidization experiment under the above conditions to obtain the same results as above.

From the foregoing, it was evidenced that even when the complex of the present invention is supported on a porous carrier, the reaction by way of the combined oxygen in the oxygen complex proceeds. In addition, as the carrier, porous carriers such as silicates, active carbon, porous glass, etc. are employable, and as the treating method after the impregnation, various methods such as passing of heated gas, low temperature calcination, etc. are employable in addition to the above filtering by suction.

COMPARATIVE EXAMPLE 1

Operations were carried out as in Examples 1, 6, 10, 16 etc. except that nitriles or organic fluorine compounds were not added. As a result, the yields of acetaldehyde and acetic acid were both less than 0.1 %. From these results, it was evidenced that nitriles and organic fluorine compounds as a modifying ligand change the specific features of the coordinated metal ion to form a stable ethylene complex and thereby contribute greatly to ethylene activation.

COMPARATIVE EXAMPLE 2

Operations and reaction were carried out as in Example 6 except that the amount of sulfolane added was varied within a range of 2 to 8 mols/l and the corresponding amounts of benzonitrile and hmpa were reduced. As a result, when the concentration of sulfolane reached 8 mols/l, acetic acid was scarcely formed and acetaldehyde alone was quantitively formed.

In the present invention, successive reactions are carried out wherein ethylene coordinated with Pd(2) and activated thereby is oxidized through the electrophilic reaction by way of oxygen of the oxo complex as an oxygen complex, and successively the resulting acetaldehyde is oxidized through the nucleophilic reaction of the combined oxygen in the superoxo complex to obtain acetic acid directly from ethylene. Accordingly the above two kinds of oxygen complexes are necessary to be present in admixture in the catalyst. If the concentration of sulfolane as a basic substance is too high, the concentration of the oxo complex increases to reduce the concentration of the superoxo complex, whereby the successive oxidation reactions of ethylene to acetaldehyde and further to acetic acid becomes difficult and acetaldehyde becomes a main product. On the other hand, the basic substance also contributes greatly to the stability of the oxygen complex.

In view of the foregoing, the amount of the basic substance added in the present invention is preferably in the range of 1 to 7 mols/l in terms of sulfolane as a representative thereof.

COMPARATIVE EXAMPLE 3

Into the same reactor as in Example 1 were fed Pd(2)Cl$_2$ (2.7 g) and hmpa (350 g) to prepare a hmpa solution of a Pd(2)Cl$_2$.(hmpa)$_2$ complex. Ethylene was passed through the solution under the same operations as in Example 1 except that no oxygen was passed, and reaction was carried out under the same conditions (60° C., 2 hours). Ethylene was not oxidized at all. Further no precipitate of metal paradium (Pd(0)) was not formed. Thus it was found that oxidation by way of Pd(2) ion did not occur.

COMPARATIVE EXAMPLE 4

To the complex solution prepared in Comparative example 3 was added Cu(1)Cl (10 g) to prepare a solution for complex catalyst. consisting of Cu(1)Cl/Pd(2)Cl$_2$/hmpa, and operations and reaction were carried out as in Comparative example 3. Ethylene oxidation was not observed at all. It was evidenced that it is necessary to pass oxygen to thereby form an oxygen complex.

COMPARATIVE EXAMPLE 5

To the catalyst solution prepared in Comparative example 4 was added benzonitrile, and operations and reaction were carried out as in Comparative example 3. In this case, too, no ethylene oxidation was observed since no oxygen was passed.

COMPARATIVE EXAMPLE 6

In Comparative example 3, oxygen was passed, but ethylene did not react at all. This evidences that ethylene oxidation reaction by means of free oxygen does not occur in the present reaction system.

From the above Comparative examples 3, 4, 5 and 6, it is evidenced that the present invention is directed to a process of directly producing acetic acid by way of oxygen-oxidization of ethylene which process is entirely different from a process using a catalyst of Pd(2)Cl$_2$—Cu(2)Cl$_2$ redox system, a process of direct oxidation with free oxygen, or the like process. In addition, when oxygen was passed through the catalyst solution containing an ethylene complex in Comparative example 5, acetic acid was obtained with almost the same yield as those in the above Examples.

From the foregoing, it is evidenced that unlike conventional processes, the present invention is directed to a novel production process wherein ethylene activated by forming an ethylene complex is oxidized by two kinds of combined oxygen (—O$_2$— and —O$_2^-$—) activated by forming oxygen complexes and having their electric charge states adjusted, to produce acetic acid at a single stage.

According to the present invention, ethylene and oxygen are not directly contacted each in the form of free molecule, but they are respectively coordinated with the respective transition metals contained in a specified composite catalyst system, and ethylene activated thereby is successively oxidized by two kinds of oxygen complexes contained in the system and having their electric charge states adjusted, whereby it is possible to produce acetic acid directly from ethylene by oxygen-oxidization at a temperature as low as room temperature and under the atmospheric pressure. Further, since the reaction is carried out under such mild conditions, the amount of by-products is small to simplify the production steps including the subsequent purification. Furthermore since oxygen is selectively absorbed even when air is used as oxygen source, all the same effectiveness as in the case where pure oxygen is used is obtained Still further, since the oxygen absorption is irreversible, it is possible to easily remove excess free oxygen after formation of the oxygen complex; hence this process has a great specific feature in the aspect of safety.

What we claim is:

1. In a process for producing acetic acid by oxygen-oxidizing ethylene in the presence of a composite catalyst solution comprising a metal complex (M$_m$X$_n$L$_l$) capable of forming oxygen-metal complexes by coordinating oxygen therewith, and a metal complex catalyst (M'$_m$, X$_n$L'$_h$) capable of forming an ethylene-metal complex by coordinating ethylene therewith, and at least one basic electron donative compound selected from the group consisting of sulfolane, dimethylsulfolane, dimethylsulfoxide, dimethylsulfone, trimethylmethane, and dimethylformamide, wherein M represents at least one transition metal selected from the group consisting of those of the group I, the groups IV to VII and the iron group of the group VIII of the Periodic Table; X represents an anion; L represents an organic phosphorus compound as a ligand; M' represents a transition metal belonging to the platinum group of the group VIII of the Periodic Table; L' represents at least one compound as a ligand selected from the group consisting of nitriles, organic fluorine compounds and organic phosphorus compounds; M, M', n and n' each represent a number determined by the valences of said transition metals and anion; and L and l' each represent the number of ligands, the improvement comprising:

adding a sufficient amount of said basic electron donative compound to the composite catalyst solution to produce the coexistence of oxo and superoxo oxygen-metal complexes in proportions suitable for maximizing the production of acetic acid.

2. A process according to claim 1, wherein the amount of said basic donative compound added to the composite catalyst solution is between about 1 to about 7 mols of sulfolane per liter of solution.

3. In a process for producing acetic acid by oxygen-oxidizing ethylene in the presence of a composite catalyst solution comprising a metal complex ($M_mX_nL_l$) capable of forming oxygen-metal complexes by coordinating oxygen therewith, and a metal complex catalyst ($M'_{m'}X_nL'_{l'}$) capable of forming an ethylene-metal complex by coordinating ethylene therewith, and at least one basic electron donative compound selected from the group consisting of sulfolane, dimethylsulfolane, dimethylsulfoxide, dimethylsulfone, trimethylmethane and dimethylformamide, wherein M represents at least one transition metal selected from the group consisting of those of the group 1, the groups IV to VII and the iron group of the group VIII of the Periodic Table; X represents an anion; L represents an organic phosphorus compound as a ligand; M' represents a transition metal belonging to the platinum group of the group VIII of the Periodic Table; L' represents at least one compound as a ligand selected from the group consisting of nitriles, organic fluorine compounds and organic phosphorus compounds; m, m', n and n' each represent a number determined by the valences of said transition metals and anion; and l and l' each represent the number of ligands, the improvement comprising:

adding a sufficient amount of said basic electron donative compound to the composite catalyst solution to produce the coexistence of oxo and superoxo oxygen-metal complexes in proportions suitable for the production of acetic acid.

4. In a process for producing acetic acid by oxygen-oxidizing ethylene in the presence of a composite catalyst solution comprising a metal complex ($M_mX_nL_l$) capable of forming oxygen-metal complexes by coordinating oxygen therewith, and a metal complex catalyst ($M'_{m'}, X_n, L'_{l'}$) capable of forming an ethylene-metal complex by coordinating ethylene therewith, and at least one basic electron donative compound selected from the group consisting of sulfolane, dimethylsulfolane, dimethylsulfoxide, dimethylsulfone, trimethylmethane, and dimethylformamide, wherein M represents at least one transition metal selected from the group consisting of those of the group I, the groups IV to VII and the iron group of the group VIII of the Periodic Table; X represents an anion; L represents an organic phosphorus compound as a ligand; M' represents a transition metal belonging to the platinum group of the group VIII of the Periodic Table; L' represents at least one compound as a ligand selected from the group consisting of nitriles, organic fluorine compounds and organic phosphorus compounds; m, m', n and n' each represent a number determined by the valences of said transition metals and anion; and l and l' each represent the number of ligands, the improvement comprising:

adding between about 1 to about 7 mols/liter of sulfolane to the composite catalyst solution to produce the coexistence of oxo and superoxo oxygen-metal complexes in proportions suitable form maximizing the production of acetic acid.

5. In a process for producing acetic acid by oxygen-oxidizing ethylene in the presence of a composite catalyst solution comprising a metal complex ($M_mX_nL_l$) capable of forming oxygen-metal complexes by coordinating oxygen therewith, and a metal complex catalyst ($M'_{m'}X_n, L'_{l'}$) capable of forming an ethylene-metal complex by coordinating ethylene therewith, and at least one basic electron donative compound selected from the group consisting of sulfolane, dimethylsulfolane, dimethylsulfoxide, dimethylsulfone, trimethylmethane, and dimethylformamide, wherein M represents at least one transition metal selected from the group consisting of those of the group I, the groups IV to VII and the iron group of the gropu VIII of the Periodic Table; X represents an anion; L represents an organic phosphorus compound as a ligand; M' represents a transition metal belonging to the platinum group of the group VIII of the Periodic Table; L' represents at least one compound as a ligand selected from the group consisting of nitriles, organic fluorine compounds and organic phosphorus compounds; m, m', n and n' each represents a number determined by the valences of said transition metals and anion; and l and l' each represent the number of ligands, the improvement comprising:

adding between about 1 to about 7 mols/liter of sulfolane to the composite catalyst solution to produce the coexistence of oxo and superoxo oxygen-metal complexes in proportions suitable for the production of acetic acid.

* * * * *